US008454566B2

(12) United States Patent
Van Antwerp

(10) Patent No.: US 8,454,566 B2
(45) Date of Patent: Jun. 4, 2013

(54) METHODS AND COMPOSITIONS FOR THE INHIBITION OF BIOFILMS ON MEDICAL DEVICES

(75) Inventor: William P. Van Antwerp, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 2618 days.

(21) Appl. No.: 10/616,784

(22) Filed: Jul. 10, 2003

(65) Prior Publication Data

US 2005/0008671 A1      Jan. 13, 2005

(51) Int. Cl.
*A61M 5/32*        (2006.01)
(52) U.S. Cl.
USPC ........................................................ 604/265
(58) Field of Classification Search
USPC ............... 604/103.02, 265, 286, 587, 288.01, 604/288.04, 287; 623/1.38, 1.46
See application file for complete search history.

(56) References Cited

U.S. PATENT DOCUMENTS

| 3,996,345 | A  | * | 12/1976 | Ullman et al. | ................ | 436/537 |
| 6,197,598 | B1 | * | 3/2001 | Schrier et al. | ................ | 436/518 |
| 6,625,479 | B1 | * | 9/2003 | Weber et al. | ................ | 600/310 |
| 2002/0082556 | A1 | * | 6/2002 | Cioanta et al. | ................ | 604/113 |

OTHER PUBLICATIONS

Gu, Ji-Dong, Belay, Brook and Mitchell, Ralph; Protection of catheter surfaces from adhesion of *Pseudomonas aeruginosa* by a combination of silver ions and lectins; World Journal of Microbiology & Biotechnology; 17:173-179, 2001.*
Andrady, Anthony L; Plastics and Environment; 2003; Wiley—IEEE, ISBN 0471095206, 9780471095200.*
Peter D Steinberg, Rene Schneider, Staffan Kjelleberg; Chemcial Defenses of Seaweeds Against Microbial Colonization; 1997; Kluwer Academic Publishers; Biodegradation 8: 211-220.*
Aitchison, E.J., et al., "Antigenic composition of an endocarditis-associated isolate of *Streptococcus faecalis* and identification of its glycoprotein antigens by ligand blotting lectins" J. Med. Micobiol., vol. 21, pp. 161-167, 1986.
Akiyama, H., et al., "Confocal laser microscopic observation of glycocalyx production by *Staphylococcus aureus* in vitro" J. of Dermatological Science, (29), pp. 54-61, 2002.
Archibald, A., et al., "The Interaction of Concanavalin A with Teichoic Acids and Bacterial Walls" Biochem. J., (123), pp. 665-667, 1971.
Cisar, J., et al., "Lectin recognition of host-like saccharide motifs in streptococcal cell wall polysaccharides" Glycobiology, vol. 5, No. 7, pp. 655-662, 1995.
Costerton, J., et al., "How Bacteria Stick" Scientific American, (238), pp. 86-95, Jan. 1978.
Coutino-Rodriguez, R., et al., "Lectins in Fruits Having Gastrointestinal Activity: Their Participation in the Hemagglutinating Property of *Escherichia coli* 0157:H7" Archives of Medical Research, (32), pp. 251-257, 2001.
Donlan, R.., "Biofilms: Micobial Life on Surfaces" Emerg Infect Dis. 8(9), pp. 881-890, Sep. 2002.

(Continued)

*Primary Examiner* — Kevin C Sirmons
*Assistant Examiner* — Bradley Osinski
(74) *Attorney, Agent, or Firm* — Gates & Cooper LLP

(57) ABSTRACT

Embodiments of the invention provide compositions which are effective to inhibit the development of biofilms on a surface of a medical device having the composition applied thereto, to medical devices having the composition applied to a surface thereof and to methods for using the compositions to coat medical devices.

14 Claims, 3 Drawing Sheets

OTHER PUBLICATIONS

Francoeur, S., et al., "New Spatially Explicit Method for Detecting Extracellular Protease Activity in Biofilms" Appl. Environ. Micobiol., vol. 67, No. 9, pp. 4329-4334, Sep. 2001.

Inbar, J., et al., "Lectins and Biocontrol" Critical Reviews in Biotechnology, vol. 17, (1), pp. 1-20, 1997.

Johnsen, A., et al., "Evaluation of Fluorescently Labeled Lectins for Noninvasive Localization of Extracellular Polymeric Substances in Sphingomonas biofilms" Appl. Environ. Micobiol, vol. 66, No. 8, pp. 3487-3491, Aug. 2000.

Leriche, V., et. al., "Use of an Enzyme-Linked Lectinsorbent Assay to Monitor the Shift in Polysaccharide Composition in Bacterial Biofilms" Appl. Environ. Micobiol., vol. 66, No. 5, pp. 1851-1856, May 2000.

Mladenov, I., et al., "Charcterisation of 20-kDa lectin-spermagglutinin from Arum maculatum that prevents Chlamydia pneumoniae infection of L-929 fibroblast cells" FEMS Immunol. Med. Microbiol., 32 (3), pp. 249-254, 2002.

Neu, T., et al., "Assessment of lectin-binding analysis for in situ detection of glycoconjugates in biofilm systems" Microbiology, (147), pp. 299-313, 2001.
Strathmann, M., et al., "Application of fluorescently labelled lectins for the visualization and biochemical characterization of polysaccharides in biofilms of *Pseudomonas aeruginosa*" J. of Microbiol. Methods, (50), pp. 237-248, 2002.
Vyas, S., et al., "Preparation, characterization and in vitro antimicrobial activity of metro-nidazole bearing lectinized liposomes for intra-periodontal pocket delivery" Pharmazie, 56 (7), pp. 554-560, Jul. 2001.
Weis, W., et al. "Structural Basis of Lectin-Carbohydrate Recognition", Annu. Rev. Biochem. (65) pp. 441-473, 1996.

* cited by examiner

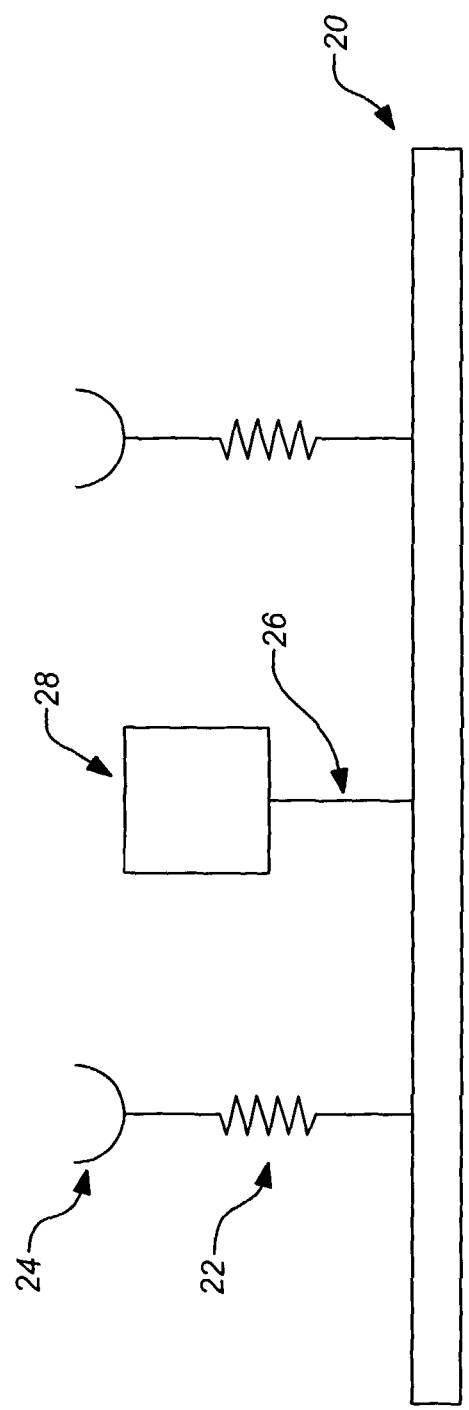

METHODS AND COMPOSITIONS FOR THE INHIBITION OF BIOFILMS ON MEDICAL DEVICES

CROSS REFERENCE TO RELATED APPLICATIONS

This application is related to U.S. patent application Ser. No. 10/260,786, POLYMER COMPOSITIONS CONTAINING BIOACTIVE AGENTS AND METHODS FOR THEIR USE, the contents of which are incorporated herein by reference.

BACKGROUND OF THE INVENTION

1. Field of the Invention

The present invention relates to compositions for coating medical devices. These compositions inhibit the growth of microorganisms and/or the formation of biofilms on the surfaces of such devices.

2. Description of Related Art

Infectious microorganisms such as bacteria, fungi and the like are capable of growing on a wide variety of living and non-living surfaces, including skin, teeth, mucosa, vascular tissue and medical devices including those implanted in-vivo. Individual microorganisms not attached to or growing on a surface are typically referred to as "planktonic". Planktonic organisms are responsible for a variety of localized and disseminated infections. When planktonic microorganisms grow and disseminate on non-living surfaces such as the surfaces of medical implants, they may cause contamination and biofouling of that surface. In many cases a microorganism can grow and accumulate on a surface to the point of becoming almost impossible to remove. This accumulation takes place through the formation of biofilms. A biofilm typically occurs when one or more microorganisms attach to a surface and secrete a hydrated polymeric matrix that surrounds them. Microorganisms existing in a biofilm, termed sessile, grow in a protected environment that insulates them from attack from antimicrobial agents. These sessile communities can give rise to nonsessile planktonic organisms, which rapidly multiply and disperse.

While planktonic organisms are typically killed by conventional antimicrobial treatments, these conventional treatments often-fail to eradicate sessile communities rooted in biofilms. This is presumably due to the fact that the slime coat generated by the sessile film physically protects the underlying organisms by limiting diffusion to the organisms and often by chemical de-activation of the bacteriological agent. For this reason, biofilms are understood to be a frequently occurring reservoir for infectious agents and pose tremendous problems for the health-care industry. The biology of biofilms is described in more detail in Bacterial biofilms: a common cause of persistent infection" J. Costerson, P. Steward, E. Greenberg, Science 284: 1318-1322 (1999).

As noted above, infections associated with implanted medical devices typically involve biofilms, where the sessile community of the biofilm provides a reservoir for an invasive infection. Antibodies and other host immune defenses can be relatively ineffective in killing the organisms contained in a biofilm even though these organisms have elicited the antibody and related immune response. In addition, while antibiotics typically treat infections caused by the planktonic organisms, they are significantly less effective at killing the sessile organisms protected in the biofilm. Consequently, once a biofilm is established on an implant such as a medical device, it is extremely difficult to treat the infection without actually removing and replacing the device. Unfortunately, even if the contaminated medical device is removed from the host, any replacement device will be particularly susceptible to contamination from the residual microorganisms in the area from which the medical device was removed.

As the difficulties associated with eliminating biofilm-based infections and contamination are well-recognized, a number of technologies have developed to prevent or impair biofilm formation. Unfortunately, biofilms continue to be a significant problem within the health care industry, in part due to ongoing difficulties in the ability to prevent organisms from establishing biofilms on the surfaces of medical devices. Consequently, there is a need in the art for methods and compositions that are effective in inhibiting the development of biofilms on the surfaces of the wide variety of medical devices that are susceptible to microbial colonization. Embodiments of the invention disclosed herein satisfy this need.

SUMMARY OF THE INVENTION

The invention disclosed herein relates generally to compositions that inhibit the formation of biofilms on medical devices, medical devices having at least one surface coated with such compositions as well as methods for coating medical devices with these compositions. The properties of these compositions can be controlled to exhibit a number of preferable characteristics including an ability to bind and/or kill pathogenic organisms. In certain embodiments of the invention, the coatings are made from one or more biodegradable materials in order to further hinder microbial colonization of a surface having that coating.

The invention disclosed herein has a number of embodiments. A preferred embodiment of the invention is a medical device having a surface coated with a composition comprising a lectin, wherein the lectin binds a compound produced by a microorganism capable of forming a biofilm on the surface of the medical device. In such embodiments of the invention, the lectin is typically disposed within (e.g. chemically coupled or entrapped) a biodegradable polymer. Optionally the biodegradable polymer used in such embodiments is a biocompatible polymer that degrades in vivo. Optionally the composition further comprises an agent that is capable of inhibiting the growth of the microorganism such as an antibiotic or an antifungal agent. Preferably the device is an implantable device such as a drug delivery pump, a pacemaker, a cochlear implant, a catheter, a shunt, a cannula or the like. In specific embodiments of the invention, the lectin included in the composition is selected to bind to a compound produced by a microorganism selected from the group consisting of *Pseudomonas aeruginosa, Streptococcus pneumoniae, Streptococcus viridans, Haemophilus influenzae, Escherichia coli, Staphylococcus aureus, Staphylococcus epidermidis* and *Candida albicans*.

A related embodiment of the invention is a biocompatible composition for coating the surface of a medical device, the composition comprising a lectin, wherein the lectin binds a compound produced by a microorganism capable of forming a biofilm on the surface of the medical device and wherein the composition further comprises a biodegradable polymer or an agent selected to inhibit the growth of the microorganism such as a biostatic or biocidal agent. In preferred embodiments, the composition comprises a biodegradable polymer and an antibiotic. A related embodiment is a method of making a biocompatible composition for coating the surface of a medical device, the method comprising combining a biodegradable polymer used to coat medical devices with a lectin selected to bind a compound produced by a microorganism capable of forming a biofilm on the surface of the medical device. In preferred embodiments, the method comprises combining this lectin composition with additional components such as substantially non-biodegradable polymers and/or antibiotic agents.

Yet another embodiment of the invention is a method for inhibiting the formation of a biofilm on the surface of a medical device; the method comprising coating the device with a composition comprising a biodegradable polymer and a lectin disposed within the biodegradable polymer, wherein the lectin is selected for the ability to bind a biofilm compound produced by a microorganism capable of forming a biofilm on the surface of the medical device. In this method, when a microorganism capable of forming a biofilm contacts the medical device, the lectin binds to the biofilm compound produced by the microorganism, thereby coupling the biofilm compound to the biodegradable polymer in a manner such that when the biodegradable polymer degrades, the biofilm sloughs away from the medical device, thereby inhibiting the formation of a biofilm on the surface of the medical device. In a preferred embodiment of the invention, the composition further comprises an agent capable of inhibiting the growth of the microorganism.

A related embodiment of the invention is a method of making a medical device having a coating that inhibits the microbial colonization of a surface of the device comprising coating the surface with a composition comprising a biodegradable polymer and a lectin coupled to the biodegradable polymer, wherein the lectin is selected to bind a compound produced by a microorganism capable of forming a biofilm on the surface of the medical device. In a preferred embodiment of the invention, the composition further comprises an antibiotic agent.

Yet another embodiment of the invention is a method of making a medical device having a coating that inhibits the microbial colonization of a surface of the device comprising coating the surface with a composition comprising a lectin selected to bind a biofilm compound produced by a microorganism capable of forming a biofilm on the surface of the medical device and an antimicrobial agent selected to kill the microorganism that produces the biofilm compound that is bound by the lectin.

BRIEF DESCRIPTION OF THE FIGURES

FIGS. 1A-1C provide illustrations of a surface of a medical device coated with a composition of the invention. The embodiment of the invention that is illustrated by these figures includes a lectin capable of being recognized and bound by a biofilm forming organism. The lectin shown in this figure is disposed in a coating that is degradable. In addition, in this embodiment of the invention the surface of the medical device includes a coating having an agent that inhibits the growth of the organism. Referring now to FIG. 1A, the surface of the medical device is represented by the numeral 20. The surface 20 includes a first polymer matrix 22, within which is disposed a lectin 24 capable of binding a biofilm compound and/or a biofilm forming organism. The surface 20 includes a second polymer matrix 26, within which is disposed one or more agents 28 that are capable of inhibiting the growth of the microorganism. Typically the agent 28 is a broad-spectrum antibiotic agent. As shown in FIG. 1B, the lectin 24 recognizes and binds a biofilm (and/or a biofilm forming organism) 30. As shown in FIG. 1B, this lectin-biofilm interaction can be used to localize the biofilm forming organism to a region of the surface 20 having one or more agents 28 that are capable of inhibiting the growth of the biofilm forming organism. As shown in FIG. 1C, the first polymer matrix 22 can be biodegradable so that the biofilm 30 bound by the lectin 24 sloughs away from the surface 20 of the medical device. In the embodiment of the invention shown in FIG. 1C, the second polymer matrix 26 having the agent 28 can be substantially nonbiodegradable so that the agent 28 remains at the surface of the medical device.

DETAILED DESCRIPTION OF THE PREFERRED EMBODIMENTS

Figure 1B:
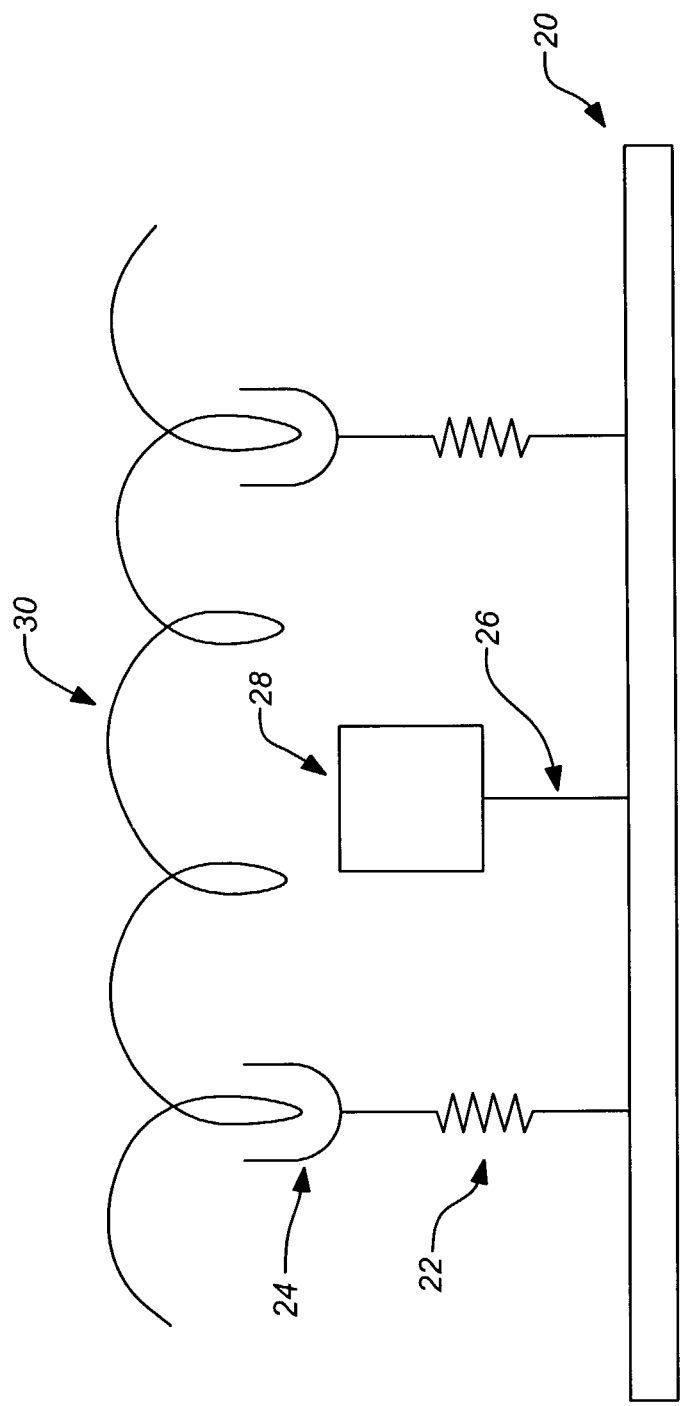

Unless otherwise defined, all terms of art, notations and other scientific terms or terminology used herein are intended to have the meanings commonly understood by those of skill in the art to which this invention pertains. In some cases, terms with commonly understood meanings are further defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as those described in see Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

Embodiments of the invention disclosed herein provide compositions for coating medical devices, medical devices having at least one surface coated with such compositions as well as methods for coating medical devices with these compositions. The properties of these compositions are controlled to exhibit a number of preferable characteristics including an ability to attract and/or kill organisms such as planktonic organisms (e.g. via molecules such as lectins and antibiotics respectively). In certain embodiments of the invention, the coatings are made from one or more erodible materials in order to further hinder an organisms colonization of a surface having that coating. In other embodiment of the invention, the lectin is used in combination with one or more antimicrobial agents that inhibit the growth of the biofilm forming organism. In addition, the coating(s) can be made to have a specific characteristics such as diffusion profiles in order to control the movement of endogenous and exogenous bioactive agents and analytes and through the coatings (e.g., biocidal agents and the like).

In accordance with a preferred embodiment of the present invention, an approach is used to provide an implantable medical device having a coating which facilitates the clearance of one or more biofilm forming organisms. The term "biofilm" is used according to its art accepted meaning and refers to microorganisms and the extracellular polymeric substance (EPS) matrix that they generate on living and nonliving surfaces as a method of cell immobilization for the microbial population(s). Briefly, as is well known in the art, microorganisms attach to surfaces and develop biofilms. Biofilm-associated cells are typically differentiated from their planktonic counterparts by generation of an extracellular polymeric substance (EPS) matrix, reduced growth rates, and the up- and down-regulation of specific genes. Attachment to a surface is a complex process regulated by diverse characteristics of the growth medium, substratum, and cell surface. An established biofilm structure typically comprises microbial cells and EPS, has a defined architecture, and provides an optional environment for the exchange of genetic material between cells. Biofilms have great importance for public health because of their role in certain infectious diseases and importance in a variety of device-related infections. See, e.g. Donlan, Emerg Infect Dis 2002 September; 8(9):881-90.

In an illustrative embodiment of the invention, the surface of the device is modified by applying a coating having a lectin capable of being recognized and bound by a biofilm forming organism. While lectins are used in preferred embodiments of the invention, molecules which act in an analogous manner and specifically bind and localize an microorganism or biofilm compounds produced by biofilm organisms to a specific region of a medical device surface are also contemplated. For example, in certain embodiments of the invention one can use antibodies or like molecules directed to specific organisms or biofilm compounds in place of lectins.

In one aspect, the present invention is directed to a biofilm inhibiting composition which may be in the form of a coating which is applied to medical devices and which substantially inhibits biofilm microorganisms from effectively colonizing (e.g. growing and proliferating) at least one surface of the medical devices and/or substantially facilitates access of antimicrobial agents to the biofilm microorganisms to assist in the prevention of the biofilm microorganisms from growing or proliferating on the at least one surface of the medical device. In these contexts, artisans will understand that such coatings may include multiple layers of materials having one or more of the agents and/or properties disclosed herein.

Broadly, the biofilm inhibiting composition typically includes a bioactive agent which inhibits biofilm formation on at least one surface of the medical device; and/or inhibits the growth or proliferation of biofilm microorganisms on at least one surface of the medical device. The biofilm inhibiting composition coating for medical devices may be formulated to substantially prevent the colonization of the device by biofilm forming microorganisms, for example by killing and/or removing substantially all of the microorganisms on the surface of medical devices. "Biofilm microorganisms" include any one of the wide variety of microorganisms which form biofilms during colonization and proliferation on the surface of medical devices, including, but not limited to, gram-positive bacteria (such as *Staphylococcus epidermidis*), gram-negative bacteria (such as *Pseudomonas aeruginosa*), and/or fungi (such as *Candida albicans*). Preferred embodiments of the invention typically target organisms including *Pseudomonad* species (e.g. *Pseudomonas aeruginosa* etc.) *Streptococcus* species (e.g. *Streptococcus pneumoniae*, *Streptococcus viridans* etc.), *Haemophilus* species (e.g. *Haemophilus influenzae* etc.), *Escherichia* species (e.g. *Escherichia coli* etc.) *Enterobacteriaceae* (e.g. *Enterobacter cloacae* etc.), *Proteus* species (e.g. *Proteus vulgaris* etc.) *Staphylococcus* species (e.g. *Staphylococcus aureus*, *Staphylococcus epidermidis* etc.), *Blastomonas*, *Sphingomonas*, *Methylobacterium* and *Nocardioides* species as well as yeast species such as *Candida albicans* etc.

In accordance with a highly preferred embodiment of the invention, a lectin is used in combination an degradable composition layer that sloughs off of the surface of a medical device that is implanted in a subject, thereby inhibiting the establishment of a biofilm colony by biofilm forming organisms. Such embodiments of the invention therefore provide a device which inhibits biofilm formation by having the organisms and biofilm compounds (e.g. the mucopolysaccharides of the biofilm) detach from the device in a manner that facilitates their clearance by the subject's physiological clearance mechanisms such as immunosurveillance and phagocytosis. In addition, as the biofilm components slough off of the device they ate made to be more accessible to immune cells (e.g. B cells, T cells, macrophages and the like) that function to further stimulate the host immune response and inhibit the growth of biofilm forming organisms.

In certain contexts, biofilms are observed to form, if at all, in a relatively short period of time. Consequently, a biodegradable polymer which inhibits the formation of biofilms during the time that devices are most susceptible to microbial colonization (e.g. the first few weeks or months immediately after implantation) can effectively reduce the establishment of a biofilm and/or incidence of biofilm formation. Consequently, certain preferred embodiments of the invention utilize devices whose coating composition includes biodegradable polymers that degrade at a specific rate within the in vivo environment in which they are placed. Illustrative embodiments are those in which greater than 50% (preferably greater than 90%) of the biodegradable polymer coating is degraded by 1 week, 2 weeks, 3 weeks, 1 month, 2 months, 3 months etc. after implantation of the medical device.

Figure 1C:
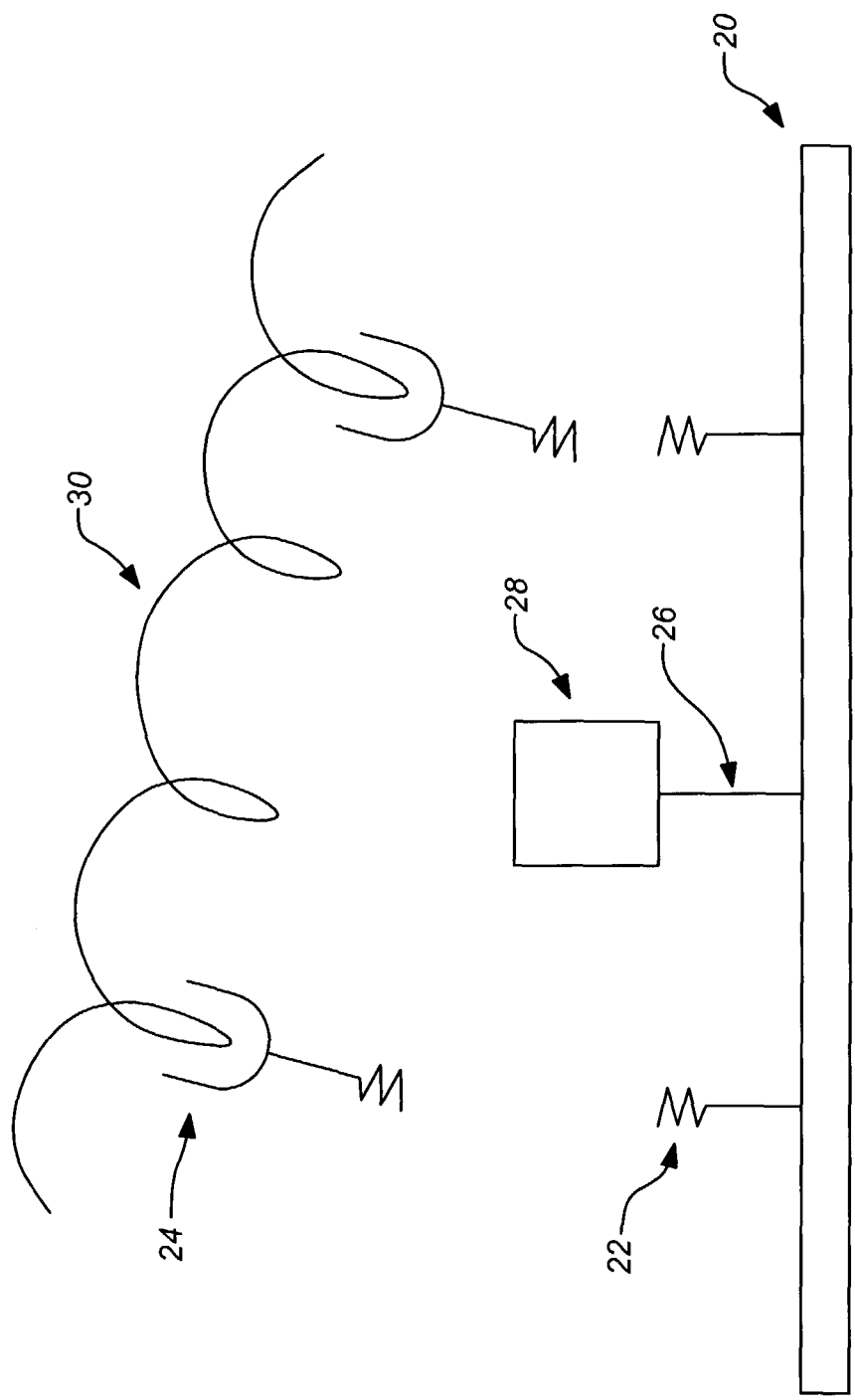

FIGS. 1A-1C provide illustrations of a surface of a medical device coated with a composition of the invention. The embodiment of the invention that is illustrated by these figures includes a lectin capable of being recognized and bound by a biofilm forming organism. The lectin coating in this embodiment of the invention is erodible. In addition, in this embodiment of the invention the coating further includes a biostatic and/or biocidal agent. Referring now to FIG. 1A, the surface of the medical device is represented by the numeral 20. The surface 20 includes a first polymer matrix 22, within which is disposed a lectin 24 capable of being recognized and bound by a biofilm forming organism. The surface 20 includes a second polymer matrix 26, within which is disposed one or more microbial growth inhibitory agents 28, typically broad-spectrum antimicrobial agents. As shown in FIG. 1B, the lectin 24 is recognizes and binds a biofilm (and/or a biofilm forming organism) 30. Typically the lectin 24 recognizes and binds a mucopolysaccharide component of a biofilm. As shown in FIG. 1B, this lectin-biofilm interaction localizes a biofilm forming organism to a region of the surface 20 having one or more agents 28 capable of inhibiting the growth of the biofilm forming organism. As shown in FIG. 1C, the first polymer matrix 22 can be biodegradable so that the biofilm 30 bound by the lectin 24 sloughs away from the surface 20 of the medical device. In the embodiment of the invention shown in FIG. 1C, the second polymer matrix 26 having the agent 28 can be selected to be less biodegradable (e.g. biodegrades at a slower rate) than polymer matrix 22 so that the agent 28 remains at the surface of the medical device after the biofilm 30 bound by the lectin 24 sloughs away from the surface 20 of the medical device.

Medical devices coated with the compositions disclosed herein are particularly useful for long-term indwelling applications due to their ability to resist biofilm formation and encrustation. As used herein, "long-term" is greater than 3 months, and preferably greater than 6 months and more preferably greater than 1 year. Subjects for treatment via implantation are preferably mammalian subjects and more preferably human subjects.

The invention disclosed herein has a number of embodiments. A preferred embodiment of the invention is a medical device having a surface coated with a composition comprising a lectin, wherein the lectin binds a compound produced by a microorganism capable of forming a biofilm on the surface of the medical device. In such embodiments of the invention, the lectin is typically disposed within (e.g. chemically coupled or entrapped) a biodegradable polymer. Optionally the biodegradable polymer used in such embodiments is a biocompatible polymer that degrades at a specific rate within an in vivo environment. Optionally the composition further comprises at least one biocidal agent such as an antibiotic or an antifungal agent. Preferably the device is an implantable device such as a drug delivery pump, a pacemaker, a cochlear implant, an analyte sensing device, a catheter, a cannula or the like. In specific embodiments of the invention, the lectin included in the composition is selected to bind to a compound produced by a microorganism selected from the group consisting of *Pseudomonas aeruginosa, Streptococcus pneumoniae, Streptococcus viridans, Haemophilus influenzae, Escherichia coli, Staphylococcus aureus, Staphylococcus epidermidis* and *Candida albicans*.

A related embodiment of the invention is a biocompatible composition for coating the surface of a medical device, the composition comprising a lectin, wherein the lectin binds a compound produced by a microorganism capable of forming a biofilm on the surface of the medical device and wherein the compositional further comprises a biodegradable polymer or an agent that inhibits the growth of the organism. Preferably, the biodegradable polymer degrades at a defined rate within an in vivo environment. In highly preferred embodiments, the composition comprises a biodegradable polymer and a biocidal agent.

A variety of permutations of the compositions disclosed herein may be generated by those skilled in the art. For example in certain embodiments of the invention the composition is composed of layers of materials, optionally having different properties. In certain embodiments of the invention, the composition comprises a plurality of lectins (e.g. wheat germ agglutinin and concanavalin A.). Preferably in such embodiments, the plurality of lectins binds a plurality of compounds produced by a plurality of microorganisms capable of forming a biofilm. In particular it is known in the art that biofilms can comprise multiple interacting microorganisms (see, e.g. Rickhard et al., Applied and Environmental Microbiology, 2000: 431-434 and Rickhard et al., Applied and Environmental Microbiology, 2002: 3644-3650). Alternatively, the plurality of lectins binds a plurality of compounds produced by a single species of microorganism. In other embodiments of the invention, the composition comprises a plurality of polymers. In other embodiments of the invention, the composition comprises a plurality of biocidal agents capable of killing plurality of microorganism species (e.g. both bacterial as well as fungal species). In illustrative embodiments, wherein the lectin and/or the biocidal agent targets a microorganism selected from the group consisting of *Pseudomonas aeruginosa, Streptococcus pneumoniae, Streptococcus viridans, Haemophilus influenzae, Escherichia coli, Staphylococcus aureus, Staphylococcus epidermidis* and *Candida albicans*.

Yet another embodiment of the invention is a method for inhibiting the formation of a biofilm on the surface of a medical device; the method comprising coating the device with a composition comprising a biodegradable polymer and a lectin disposed within the biodegradable polymer, wherein the lectin is selected for the ability to bind a biofilm compound produced by a microorganism capable of forming a biofilm on the surface of the medical device. In this method, when a microorganism capable of forming a biofilm contacts the medical device, the lectin binds to the biofilm compound produced by the microorganism, thereby coupling the biofilm compound to the biodegradable polymer in a manner such that when the biodegradable polymer degrades, the biofilm sloughs away from the medical device, thereby inhibiting the formation of a biofilm on the surface of the medical device. Preferably, the biodegradable polymer is selected to degrade at a defined rate within an in vivo environment.

In a preferred embodiment of the invention, the composition comprises an agent that inhibits the growth of the microorganism and/or the formation of the biofilm. Optionally the composition further comprises a substantially non-biodegradable polymer and wherein this inhibitory agent is disposed with the substantially non-biodegradable polymer such that when the biodegradable polymer degrades, the inhibitory agent remains on the surface of the medical device. In preferred embodiments of the invention, the composition is composed of layers of materials, for example a first layer which includes a lectin and a second layer which includes an inhibitory agent. Preferably the device coated by such methods is an implantable device such as a drug delivery pump, a pacemaker, a cochlear implant, a catheter, a shunt (e.g. a cerebral or spinal shunt), a cannula or the like.

In certain embodiments of the invention, the coating composition includes a lectin that inherently inhibits biofilm formation. For example, a lectin which competitively binds to moiety within the extracellular polymeric substance that is involved in the formation of the biofilm may compromise the integrity of the biofilm complex by disrupting the interaction of biofilm components. Alternatively, the formation of a biofilm may be inhibited when such a lectin preferentially directs the extracellular polymeric substance away from the area and/or environment targeted by the microorganism. An illustrative embodiment of this includes medical device having a surface coated with a composition comprising a lectin, wherein the lectin is selected to inhibit the formation of a biofilm on the surface of the medical device. A related embodiment is a method for inhibiting the formation of a biofilm on the surface of a medical device, the method comprising coating the device with a composition comprising a lectin selected for the ability to inhibit the formation of a biofilm on the surface of the medical device.

A related embodiment of the invention is a method of making a medical device having a coating that inhibits the microbial colonization of a surface of the device comprising coating the surface with a composition comprising a biodegradable polymer and a lectin coupled to the biodegradable polymer, wherein the lectin is selected to bind a compound produced by a microorganism capable of forming a biofilm on the surface of the medical device. In a preferred embodiment of the invention, the composition further comprises a biocidal agent.

Yet another embodiment of the invention is a method of making a medical device having a coating that inhibits the microbial colonization of a surface of the device comprising coating the surface with a composition comprising a lectin selected to bind a biofilm compound produced by a microorganism capable of forming a biofilm on the surface of the medical device; and an antimicrobial agent selected to kill the microorganism that produces the biofilm compound that is bound by the lectin.

In a specific illustrative embodiment of the invention, the surface coated by the composition is titanium, a material that is commonly used in medical devices and the composition includes a polylactide formulation, for example microspheres of polylactide coated with a lectin. In this embodiment, the lectin is concanavalin A, wheat germ agglutinin or a lectin derived from Helix aspersa, *Phaseolus vulgaris* or *Trichamonas vulgaris* (see, e.g. Francoeur et al., Appl Environ Microbiol 2001, 67(9): 4329-34; Neu et al., Microbiology, 2001 147(pt 2): 299-313; and Appl Environ Microbiol 2000, 66(8): 3487-91). Such lectins are commercially available from a number of sources such as Sigma Chemical, Company (e.g. Sigma catalog numbers L9640, L6655, L8629, L9040; and C2010). In this embodiment of the invention, the composition further includes the antibiotic streptomycin. In this embodiment, the lectin serves to target the biofilm forming organism to a portion of the device that has a biocidal agent (streptomycin) that will kill the organism. In the same manner the lectin therefore facilitates the attachment of the biofilm forming organism to a portion of the device that will slough off in a manner that further inhibits biofilm formation. In such contexts, biofilm formation is inhibited in part by treating the surface of a medical device with a degradable composition that has a greater affinity for biofilms than does the untreated surface of the device.

Various embodiments and aspects of the invention are described in detail below.

Illustrative Compositions for Forming Coatings on Medical Devices

Compositions of the invention can include essentially any one of the wide variety of materials (typically polymers) that are compatible with medical devices, particularly implanted devices. Polymers may be crosslinked or uncrosslinked, linear or branched, natural or synthetic, thermoplastic or thermosetting, or biostable, biodegradable, bioabsorbable or dissolvable. Embodiments of the invention described herein include various types of polymer coatings for coating implantable medical devices such as drug delivery pumps, cochlear implants, stents, cannulae, and the like that include growth inhibitory agents such as antibiotic agents. Typically, polymers are applied to the surface of an implantable device by methods such as spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device.

Exemplary polymers include but are not limited to the following molecules: polycarboxylic acid polymers and copolymers including polyacrylic acids (e.g., acrylic latex dispersions and various polyacrylic acid products such as HYDROPLUS, available from Boston Scientific Corporation, Natick Mass. and described in U.S. Pat. No. 5,091,205, the disclosure of which is hereby incorporated herein by reference, and HYDROPASS, also available from Boston Scientific Corporation); acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polybismaleinimides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); anhydride polymers and copolymers including maleic anhydride polymers; polymers and copolymers of vinyl monomers including polyvinyl alcohols, polyvinyl halides such as polyvinyl chlorides, ethylene-vinylacetate copolymers EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes flow and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylenetetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Preferred polymers for use in connection with the present invention include ethylene-vinyl acetate copolymers (EVA) and polyurethanes and hydrogels. A hydrogel is a highly-interdependent, biphasic matrix consisting of a solid component (usually a polymer, and more commonly a highly cross-linked polymer) that has both hydrophilic and hydrophobic character. Additionally, the matrix has a liquid component (e.g., water) that is retained in the matrix by intermolecular forces. The hydrophobic character provides the matrix with a degree of water insolubility while the hydrophilic character affords water permeability. The polymer portion of the hydrogel will contain functionality which is suitable for hydrogen bonding (e.g., hydroxyl groups, amino groups, ether linkages, carboxylic acids and esters, and the like). Moreover, the affinity for water presented by the hydrogen bonding functionality must be of sufficient degree that the hydrated hydrogel will retain the water within its matrix even upon placement of the hydrogel in a hydrophobic medium such as an oil or lipid matrix. In addition to this binding of water within the hydrogel matrix, the hydrogel should allow water to flow through it when placed in an aqueous environment. Exemplary hydrogels are disclosed in U.S. Pat. Nos. 6,462,162, 5,786,439, and U.S. Pat. No. 5,770,060 which are incorporated herein by reference.

Hydrogels used in coating the implantable devices typically include a polyurea, a polyurethane or a polyurethane/polyurea combination. As used herein, the term "polyurethane/polyurea" refers to a polymer containing urethane linkages, urea linkages or combinations thereof. Typically, such polymers are formed by combining diisocyanates with alcohols and/or amines. For example, combining isophorone diisocyanate with PEG 600 and 1,4-diaminobutane under polymerizing conditions provides a polyurethane/polyurea composition having both urethane (carbamate) linkages and urea linkages. Such hydrogels are typically prepared from the reaction of a diisocyanate and a hydrophilic polymer, and optionally, a chain extender. The hydrogels can be extremely hydrophilic and can have a water pickup of from about 25% to about 400% by weight, more preferably from about 150% to about 400%.

The diisocyanates which are useful in this aspect of the invention are those which are typically used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6-hexamethylene diisocyanate (HDI), trimethylhexamethylene diisocyanate (TMDI), trans-1,4-cyclohexane diisocyanate (CHDI), 1,4-cyclohexane bis(methylene isocyanate) (BDI), 1,3-cyclohexane bis(methylene isocyanate) ($H_6XDI$), isophorone diisocyanate (IPDI) and 4,4'-methylenebis(cyclohexyl isocyanate) ($H_{12}MDI$). In preferred embodiments, the diisocyanate is an aliphatic diisocyanate, more preferably isophorone diisocyanate, 1,6-hexamethylene diisocyanate, or 4,4'-methylenebis(cyclohexyl isocyanate). A number of these diisocyanates are available from commercial sources such as Aldrich Chemical Company Milwaukee, Wis., USA) or can be readily prepared by standard synthetic methods using literature procedures.

In preferred embodiments of the invention, the coat composition includes a polymer designed to degrade in a manner that sloughs organisms off a surface that they are attempting to colonize. A number of such polymers are known in the art and are generally termed biodegradable One type of degradation is bulk degradation, in which the polymer degrades in a fairly uniform manner throughout the matrix. The prevailing mechanism of bulk degradation is hydrolysis of the hydrolytically unstable polymer backbone. First, water penetrates the bulk of the solid polymeric implant, preferentially attacking chemical bonds in the amorphous phase and converting long polymer chains into shorter water-soluble fragments. This results, initially, in a reduction in molecular weight ($M_n$) without an immediate change in physical properties. A second type of degradation is surface erosion, typically called bioerosion. Bioerosion can occur when the rate at which water penetrates the coating of the implant is slower than the rate of the conversion of the polymer into water-soluble materials. Bioerosion results in a thinning of the implant coating over time.

Commonly used biodegradable polymers are typically of the poly(hydroxyacid) type, in particular poly(L-lactic acid), poly(D,L-lactic acid), poly(glycolic acid), and copolymers thereof. A typical copolymer is poly(lactide-co-glycolide), abbreviated as PLGA. These materials are broken down in the body to the non-toxic products lactic acid and glycolic acid, and have been approved by the Food and Drug Administration for use as resorbable sutures, in bone implants, and as controlled release microspheres. Other polymers being utilized include poly(funimaric anhydride) and poly(sebacic anhydride). Mathiowitz, E., Jacob, J. S., Jong, Y. S., Carino, G. P., Chickering, D. E., Chaturvedi, P., Santos, C. A., Vijayaraghavan, K., Montgomery, S., Bassett, M. and Morrell, C., Biologically Erodible Microspheres as Potential Oral Drug Delivery Systems, Nature, 386:410-414, 1997. The use of polymeric microspheres for controlled drug delivery has been the subject of a number of reviews. Langer, R., Cima, L. G., Tamada, J. A. and Wintermantel, E.: "Future Directions in Biomaterials," Biomaterials, 11:738-745, 1990.

Additional illustrative bioerodable and/or biodegradable polymers include polymers and copolymers of: poly(anhydride), poly(hydroxy acid)s, poly(lactone)s, poly(trimethylene carbonate), poly(glycolic acid), poly(lactic acid), poly(glycolic acid)-co-poly(glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Preferred bioerodable polymers include poly(lactic acid), poly(glycolic acid), poly(lactide), poly(glycolide), poly(lactide-co-glycolide)s, poly(caprolactone), polycarbonates, polyamides, polyanhydrides, poly(amino acid)s, poly(ortho ester)s, polyacetals, polycyanoacrylates, poly(ether ester)s, poly(dioxanone)s, poly(alkylene alkylate)s, copolymers of poly(ethylene glycol) and poly(ortho ester), degradable polyurethanes and copolymers and blends thereof. Illustrative bioerodable polymers are further described in U.S. patent application Nos. 20020015720 and 20020034533.

Polymers can be designed to have additional desirable properties such as exhibiting rate controlled release of therapeutic agents or other agents. A wide variety of microencapsulation drug delivery systems have been developed using such polymers for the rate controlled release of therapeutic agents or other agents. For instance, considerable research has been devoted to incorporating therapeutic agents into polyesters such as poly-ϵ caprolactone), poly(ϵ-caprolactone-Co-DL-lactic acid), poly(DL-lactic acid), poly(DL-lactic acid-Co-glycolic acid) and poly(ϵ-caprolactone-Co-glycolic acid) in which release was diffusion controlled. See, for example, Pitt, C. G., Gratzl, M. M., Jeffcoat, A. R., Zweidinger, R., Schindler, A., "Sustained Drug Delivery Systems. II. Factors Affecting Release Rates from Poly(ϵ-caprolac-tone) and Related Biodegradable Polyesters", J. Pharm. Sci., 68, 1534 (1979). Degradation of the polyesters has been reported to proceed by random hydrolytic cleavage of ester linkages by an autocatalytic process with the rate of chain cleavage being influenced by chemical and morphological factors.

As is known in the art, the polymer compositions described herein can be used as a scaffolding which can be manipulated to add additional polymer components, bioactive agents, reactive chemical groups and the like. Various polymers and bioactive agents that can be incorporated into the polymer composition scaffolding are described in detail below. In addition, polymers having organic acid functional groups (e.g. carboxylic acid or sulfonic acid) are illustrative embodiments of this aspect of the invention (see e.g. U.S. Pat. No. 6,231,600). In the present context the term "organic acid group" is meant to include any groupings which contain an organic acidic ionizable hydrogen, such as carboxylic and sulfonic acid groups. The expression "organic acid functional groups" is meant to include any groups which function in a similar manner to organic acid groups under the reaction conditions, for instance metal salts of such acid groups, particularly alkali metal salts like lithium, sodium and potassium salts, and alkaline earth metal salts like calcium or magnesium salts, and quaternary amine salts of such acid groups, particularly quaternary ammonium salts.

Polymer having organic acid functional groups, can be included in a first or subsequent aqueous coating composition, and can be selected with due regard for the nature of the substrate to be coated. Typically a polymer in a first coating composition will be selected from homo- and co-polymers including vinylic monomer units, polyurethanes, epoxy resins, and combinations thereof. A polymer in the first coating composition is preferably selected from polyurethanes, polyacrylates, polymethacrylates, poly-isocrotonates, epoxy resins, acrylate-urethane co-polymers, and combinations thereof having organic acid functional groups. In a particularly preferred embodiment of methods of the invention, a polymer in the first coating composition is selected from homo- and co-polymers having a substantial amount of organic acid functional groups in their structure, which may act as an internal emulsifier. A class of polyurethanes which may be used in the first coating composition are the so-called water-borne polyurethanes, among which are the so-called internally emulsified water-borne polyurethane containing carboxylic acid groups and/or sulfonic acid groups, optionally as salts of such groups, as internal emulsifiers are particularly preferred.

The polymer matrix portion can be formed using various known processes. For example, the polymer matrix portion can be formed using solvent-based techniques in which the polymer is first dissolved in a solvent, after which the polymer solution is used to form the matrix portion. The solvent should, of course, be compatible with the polymer. Preferred techniques of this nature include solvent casting, spin coating, web coating, solvent spraying, dipping, fiber forming, ink jet techniques and combinations of these processes. If desired, coating techniques can be repeated or combined to build up the polymer matrix portion to the desired thickness. In many cases, the solution is applied to a template, and the polymer matrix portion is obtained, after solvent elimination, by simply removing the polymer from the template. Such techniques are particularly appropriate for forming simple objects such as sheets, tubes, cylinders and so forth.

When forming the matrix portion using solvent-based techniques, so long as it is compatible, the bioactive agent can be provided within the polymer/solvent mixture, for example, in dissolved form or as a particulate suspension. Such techniques allow the bioactive agent to be loaded concurrently with polymer matrix formation.

As another example, the polymer matrix can be provided in final shape by casting processes in which a mold or other receptacle is provided with liquid monomer, whereupon the monomer becomes cured (for example by the application of heat, ultraviolet light, atmospheric exposure, etc.) Similar to solvent-based techniques, so long as the bioactive agent is compatible with the liquid monomer, the bioactive agent can be provided within the liquid monomer at the time of polymer matrix formation, allowing the bioactive agent to be loaded concurrently with polymer matrix formation.

As yet another example, in the case where a thermoplastic polymer is selected as the polymer matrix material, a variety of standard thermoplastic processing techniques for device formation can be used, including compression molding, injection molding, blow molding, spinning, vacuum forming and calendaring, thermoforming and rotational molding, as well as extrusion into sheets, fibers, rods, tubes and other cross-sectional profiles of various lengths. Assuming that the bioactive agent to be loaded within the matrix is stable at processing temperatures, then it can be combined with the polymer prior to thermoplastic processing, for example, by extrusion (see, e.g. U.S. Pat. No. 4,917,686)

The bioactive agent can also be provided within the polymer matrix after the polymer matrix portion is formed, for example, using one of the techniques described above. For instance, the bioactive agent can be first dissolved in a solvent that is compatible with both the polymer matrix and the bioactive agent. Subsequently, the thus-formed solution is contacted with the polymer matrix portion, whereupon the bioactive agent is loaded into the polymer matrix portion, for example, by diffusion into the matrix. For this purpose, the polymer matrix portion can be immersed or dipped into the solution; the solution can be applied to the polymer matrix, for example, by spraying; and so forth. The polymer matrix portion can subsequently be dried, with the bioactive agent remaining therein.

It may be useful to coat a first polymer matrix portion with one or more additional polymer layers, which can serve, for example, as a barrier layer to retard diffusion of the bioactive agent and extend release time. For example, a barrier layer may be selected from those polymer materials discussed above that are effective to retard diffusion. Other techniques for extending the release time of the bioactive agent include maximizing polymer matrix depth and choosing bioactive agents with low solubility.

Bioactive Components

The polymer compositions and methods of making and using them that are described herein can be used to incorporate a wide variety of bioactive agents that are known in the art (see e.g., Sigwatt et al., J Invasive Cardiol 2001 February; 13(2):141-2; discussion 158-70; Chan et al., Update on Pharmacology for Restenosis, Curr Interv Cardiol Rep. 2001 May; 3(2):149-155; and Hofma et al., Recent Developments in Coated Stents, Curr Interv Cardiol Rep. 2001 February; 3(1):28-36). In preferred embodiments of the invention, the bioactive component is a lectin selected to bind an organism capable of establishing biofilms on the surfaces of medical implants. In highly preferred embodiments of the invention, coating includes a biocidal agent selected to inhibit the growth of and/or kill organisms capable of establishing biofilms on the surfaces of medical implant.

Preferred embodiments of the coat compositions includes a lectin capable of binding to a biofilm forming organism. As used herein, a "lectin" is used according to its art accepted meaning and refers to the wide variety of proteins known in the art as being capable of binding cells such as bacterial and/or yeast cells. For selected general references describing such macromolecules, see, e.g. Callow, J. A. and J. R. Green (eds.) 1992, Perspectives in Cell Recognition, Cambridge Univ. Press, Cambridge; Weis et al., Annu Rev Biochem 1996, 56: 441-473; Inbar et al., Crit Rev Biotechnol 1997, 17(1): 1-20; Archibald et al., Biochem J 1971, 123(4): 665-667; Costerton et al., 1978, How bacteria stick? Sci. Am. (January) 238: 86-95; Ofek, I. and R. J. Doyle 1994, Bacterial Adhesion to Cells and Tissues, Chapman and Hall, NY.; Pueppke, S. G. 1984. Adsorption of bacteria to plant surfaces, pp. 215-261 in Plant Microbe Interactions, Vol. 1; Pusztai, A. 1991, Plant Lectins. Cambridge Univ. Press, Cambridge; Van Damme, E. J. M. et al. 1998, Handbook of Plant Lectins: Properties and Biomedical Applications, Published Chichester; New York: John Wiley; Van Damme, E. J. M., R. J. Doyle and M. Slifkin eds. c1994; and Lectin-microorganism Interactions, Published New York: M. Dekker the contents of each of which is incorporated herein by reference. In addition, a variety of lectins which bind specific pathogens (e.g. *Pseudomonas, Staphylococcus, Streptococcus, Escherichia* and *Chlamydia* species) are known in the art. For selected references describing such molecules see, e.g. Strathmann et al., J Microbiol Methods 2002, 50(3): 237-248; Akiyama et al., J Dermatol Sci 2002, 29(1): 54-61; Cisar et al., Glycobiology 1995, 5(7): 655-662; Coutino-Rodriguez et al., Arch Med Res 2001, 32(4): 251-257; Aitchison et al., J Med Microbiol 1986, 21(2): 161-167; and Mladenov et al., FEMS Immunol Med Microbiol 2002, 32(3): 249-254, the contents of each of which is incorporated herein by reference.

Lectins are proteins produced by plants and some animal species that bind specifically and non-covalently to sugar groups that are present on the surface of microbial cells. Typical lectins for use with various embodiments of the invention include but are not limited to: concanavalin A, wheat germ agglutinin, abrin, phytohaemagglutinin, limulin, or one of the lectins produced by the following species: *Agaricus bisporus, Anguilla anguilla, Arachis hypogaea, Bandeiraea simplicifolia, Baubinia purpurea, Caragana arborescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Lycopersicon esculentum, Maclura pomifera, Momordica charantia, Mycoplasma gallisepticum, Naja mocambique, Naja kaouthia, Perseau americana, Phaseolus coccineus, Phaseolus limensis, Phaseolus vulgaris, Phytolacca americana, Pisum sativum, Pseudomonas aeruginosa, Psophocarpus tetragonolobus, Ptilota plumosa, Ricinus communis, Robinia pseudoacacia, Sambucus nigra, Solanum tuberosum, Sophora japonica, Tetragonolobus purpureas, Triticum vulgaris, Ulex europaeus, Vicia faba, Vicia sativa, Vicia villosa, Vigna radiata, Viscum album*, and *Wisteria floribunda*.

A number of assays for examining the interaction between lectins and microorganisms are known in the art. Typically such assays comprise an analysis of the ability of a microorganism to bind to a matrix coated with a test lectin (e.g. a test lectin coated latex bead) in a physiological medium (e.g. phosphate buffered saline) and then comparing the level of microbial binding that is observed with the test lectin to that observed with a comparable uncoated matrix and/or a matrix coated with a lectin known to bind that microorganism (e.g. negative and positive controls respectively). Consequently, any lectin known in the art and/or any newly discovered lectin can be readily examined for its ability to bind one or more microbial species. In addition, a variety of procedures such as avidin-biotin based lectin binding assays are described in U.S. patent application Nos. 20020137674 20020103263 and 20020111297. Leriche et al., Appl Environ Microbiol 2000 May; 66(5):1851-6 describe a enzyme-linked lectinsorbent assay (ELLA) to monitor the shift in polysaccharide composition in bacterial biofilms. Johnsen et al., Appl Environ Microbiol 2000 August; 66(8):3487-91 describe the evaluation of fluorescently labeled lectins for noninvasive localization of extracellular polymeric substances in Sphingomonas biofilms. Vyas et al., Pharmazie 2001 July; 56(7):554-60 describe a bovine submaxillary mucin (BSM) binding assay in the characterization of lectinized liposomes for intra-periodontal pocket delivery. The contents of each of these disclosures are incorporated herein by reference.

Preferred embodiments of the coat compositions includes a biocidal agent capable of inhibiting the growth of a biofilm forming organism. As used herein, an "biocidal agent" is any agent that is harmful to biofilm forming microbes, especially pathogenic bacteria. Suitable biocidal agents that may be included in the coating include, but are not limited to, antimicrobial, antibiotics, antimyobacterial, antifungals, antivirals, and the like. Preferred antimicrobial agents include but are not limited to the biquanides such as chlorhexidine, polymyxins, tetracyclines, aminoglycosides, rifampicin, bacitracin, neomycin, chloramphenicol, miconazole, quinolones, penicillins, nonoxynol 9, fusidic acid, cephalosporins, mupirocin, metronidazole, cecropins, protegrins, bacteriocins, defensins, nitrofurazone, mafenide, vancomycins, clindamycins, lincomycins, sufonamides, norfloxacin, pefloxacin, nalidixic acid, oxolinic acid (quinalone), enoxacin, ciprofloxacin, and fusidic acid and combinations thereof. Preferred broad-spectrum antimicrobial agents for the present invention include triclosan, chlorhexidine, silver sulfadiazine, silver ions, benzalkonium chloride, and zinc pyrithione, as well as broad-spectrum antibiotics such as quinolones, fluoroquinolones, aminoglycosides and sulfonamides, and antiseptics such as iodine, methenamine, nitrofurantoin, validixic acid and other acidifying agents, including acids extracted from cranberry juice and combinations thereof.

Certain embodiments of the invention include coatings having multiple bioactive agents including more than one lectin and/or more than one biocidal agent. For example, preferred embodiments of the invention include coatings having multiple lectins which recognize multiple organisms capable of forming biofilms. In this context, certain embodiment of the invention utilize multiple target biocidal agents such as an antibiotic and an antifungal agent in order to inhibit the formation of biofilms comprising mixed species such as *Candida albicans* and *Staphylococcus epidermidis* (see, e.g. Adam et al., J Med Microbiol 2002 April; 51(4):344-9). Other preferred embodiments of the invention include coatings having multiple biocidal agents having differing properties. For example, one embodiment of the invention provides compositions having both a fast-acting antimicrobial agent and a long-lasting antimicrobial agent. The combined effect of the antimicrobial agents reduces microbial infection and resistance.

A number of assays for examining the biocompatibility of various compositions are known in the art. Consequently, any permutation of the inventive compositions disclosed herein can be readily examined to assess its biocompatibility profile. For example, U.S. Pat. No. 4,760,020 describes an in vitro assay for biocompatibility. Johnson et al., J Biomed Mater Res. 1985 May-June; 19(5):489-508 describe biocompatibility test procedures for materials evaluation in vitro. Courey et al., J Biomater Appl 1988 October; 3(2):130-79 describe factors and interactions affecting the performance of polyurethane elastomers in medical devices. Tarnok et al., Cytometry 1999 February 15; 38(1):30-9 describe a rapid in vitro biocompatibility assay of endovascular stents by flow cytometry using platelet activation and platelet-leukocyte aggregation. Geckeler et al., Naturwissenschaften 2000 August; 87(8): 351-4 describe a biocompatibility correlation of polymeric materials using human osteosarcoma cells. The contents of each of these disclosures is incorporated herein by reference. In addition, a number of commercially available biocompatibility assays are known in the art which can be used to examine certain embodiments of the invention, for example the CytoTox 96™ Assay sold by Promega (see, e.g. *Promega Notes Magazine* Number 45, 1994, p. 7).

The bioactive agents used in the polymers described herein can be prepared and/or modified according to a wide variety of techniques known in the art such as being encapsulated in liposomes. For example U.S. Pat. No. 6,200,599 teaches nucleic acids of all types may be associated with the compounds described therein and liposomes. These include DNA, RNA, DNA/RNA hybrids (each of which may be single or double stranded), including oligonucleotides such as antisense oligonucleotides, chimeric DNA-RNA polymers, and ribozymes, as well as modified versions of these nucleic acids wherein the modification may be in the base, the sugar moiety, the phosphate linkage, or in any combination thereof. In addition, these include synthetic oligonucleotides involved in the induction of the sequence-specific RNA interference (RNAi) activity in cells (see, e.g. Hohjoh, FEBS Lett 2002 June 19; 521(1-3):195-9). Antisense oligonucleotides may be constructed to inhibit expression of a target gene such as one expressed by cells colonizing the surface of an implant.

Liposome formulations can also be used to deliver a broad range of conventional pharmaceuticals and therapeutic drugs. In addition to the aforementioned nucleic acids, in certain aspects, the liposome formulations of the present invention comprise small organic or inorganic compounds as bioactive agents. In certain embodiments, the liposomal formulations can encapsulate a bioactive agent and then release the encapsulated contents upon mild acidic conditions. For example, U.S. Pat. No. 6,200,599, describes the release of encapsulated calcein upon lowering the pH. Thus, the liposomal formulations comprising a pH-sensitive compound can advantageously be used to entrap, release and deliver therapeutic agents.

As discussed below, the bioactive agents may be entrapped within the polymer compositions or coupled to the polymer compositions using one or more the techniques for generating such compositions known in the art.

Preparation and Manipulation of Polymer Compositions

The polymer coating preparations described herein can be prepared by methods typically employed in the art. For example, polymerization of the reactants can be carried out in bulk or in a solvent system. Use of a catalyst is preferred, though not required. Suitable catalysts include dibutyltin bis(2-ethylhexanoate), dibutyltin diacetate, triethylamine and combinations thereof. Preferably dibutyltin bis(2-ethylhexanoate is used as the catalyst. Bulk polymerization is typically carried out at an initial temperature of about 25° (ambient temperature) to about 50° C., in order to insure adequate mixing of the reactants. Upon mixing of the reactants, an exotherm is typically observed, with the temperature rising to about 90°-120° C. After the initial exotherm, the reaction flask can be heated at from 75° C. to 125° C., with 90° C. to 100° C. being a preferred temperature range. Heating is usually carried out for one to two hours. Polymers prepared by bulk polymerization are typically dissolved in dimethylformamide and precipitated from water. Polymers prepared in solvents such as THF can be poured into water at ambient temperatures, then filtered, dried, washed with boiling water and re-dried.

Solution polymerization can be carried out in a similar manner. Solvents which are suitable for solution polymerization include, tetrahydrofuran, dimethylformamide, dimethyl sulfoxide, dimethylacetamide, halogenated solvents such as 1,2,3-trichloropropane, and ketones such as 4-methyl-2-pentanone. Preferably, THF is used as the solvent. When polymerization is carried out in a solvent, heating of the reaction mixture is typically carried out for at least three to four hours, and preferably at least 10-20 hours. At the end of this time period, the solution polymer is typically cooled to room temperature and poured into DI water. The precipitated polymer is typically collected, dried, washed with hot DI water to remove solvent and unreacted monomers, then re-dried. The dried polymer can be evaluated for water pickup as described for example in U.S. Pat. No. 5,786,439 and U.S. Pat. No. 5,777,060. In certain embodiments of the invention, the hydrogels of the invention will have a water pickup of at least 120%, preferably 150% to about 400%, and more preferably about 200% to about 400%. An illustrative embodiment of the invention includes a polymer coating having a water pickup of from about 25% to about 400% by weight. In a related embodiment, the polymer coating has a glucose diffusion coefficient of from about $1 \times 10^{-9}$ cm$^2$/sec to about $200 \times 10^{-9}$ cm$^2$/sec, and a ratio of $D_{oxygen}/D_{glucose}$ of from about 5 to about 2000, or optionally, from about 5 to about 200.

As discussed herein, the reactants and reaction conditions used to generate the polymer compositions disclosed herein can be modified to alter the properties of the final polymer composition. For example, properties such as the diffusion coefficients (e.g. the rate at which molecules such as endogenous and exogenous analytes are able to diffuse through the polymer matrix), the rate of degradation of one or more of the polymer components or the rates of the release of a bioactive agent(s) can be manipulated by manipulating the reaction conditions (and hence the final polymer composition properties) used to generate the polymers.

From the above description, it will be apparent to one of skill in the art that the discovery underlying the present invention is the use of polymer compositions such as silicon-containing polymers, such as siloxanes, which incorporate biofilm inhibiting bioactive agents in the formation of biocompatible coatings. For example, silicon-containing polymers are used in conjunction with (e.g. covalently attached to) other compounds such as hydrophilic polymers, compounds having reactive groups and bioactive compositions for the preparation of coatings in which the movement of analytes and reactive species can be controlled by varying the amounts of each component. The coatings produced from these components are typically homogeneous and are useful for coating a number of devices designed for in vivo implantation. Once polymers have been prepared having suitable properties, the polymers can be solubilized in a solvent and used to coat a implantable device.

Preparation of coated implantable devices is typically accomplished by dissolving the dried polymer in a suitable solvent and spin-coating the medical device, typically using, for example, a 5 wt % in 2-propanol solution of the polymer. The selection of other suitable solvents for coating the medical devices will typically depend on the particular polymer as well as the volatility of the solvent. Other suitable solvents include THF, CHCl$_3$, CH$_2$Cl$_2$, DMF or combinations thereof. More preferably, the solvent is THF or DMF/CH$_2$Cl$_2$.

A preferred method of modulating the properties of the polymer compositions disclosed herein is to control the diffusion coefficient (which relates to the rate at which a compound diffuses through a coating matrix) of the one or more polymer coating layers. In this context, analyte diffusion coefficients can be determined for the coating compositions of the present invention. Methods for determining diffusion coefficients are known to those of skill in the art, and are described for example in U.S. Pat. No. 5,786,439 and U.S. Pat. No. 5,777,060.

An illustrative method of coating a medical device includes sequentially applying a plurality of relatively thin outer layers of a coating composition comprising a solvent mixture of polymeric silicone material and crosslinker and, optionally a biologically active species (see, e.g. U.S. Pat. No. 6,358,556). The coatings can be cured in situ and the coated, cured prosthesis can be sterilized in a step that includes preferred pretreatment with argon gas plasma and exposure to gamma radiation electron beam, ethylene oxide, steam.

In this context, embodiments of the present invention provides processes for producing a relatively thin layer of biostable elastomeric material in which an amount of biologically active material is dispersed as a coating on the surfaces of a medical device such as a stent. The preferred stent to be coated is a self-expanding, open-ended tubular stent prosthesis. Although other materials, including polymer materials, can be used, in the preferred embodiment, the tubular body is typically formed of an open braid of fine single or polyfilament metal wire which flexes without collapsing and readily axially deforms to an elongate shape for transluminal insertion via a vascular catheter. The stent resiliently attempts to resume predetermined stable dimensions upon relaxation in situ.

The polymer coating is preferably applied as a mixture, solution or suspension of polymeric material and one or more biologically active species dispersed in an organic vehicle or a solution or partial solution of such species in a solvent or vehicle for the polymer and/or biologically active species. Optionally different biological species are placed within different polymer layers. The bioactive material(s) is dispersed in a carrier material which may be the polymer, a solvent, or both. The coating is preferably applied as one or more relatively thin layers that are applied sequentially. In some applications the coating may further be characterized as an undercoat and a topcoat. The coating thickness ratio of the topcoat to the undercoat may vary with the desired effect and/or the elution system. Typically these are of different formulations.

In an illustrative embodiment of a device having a plurality of coating layers, the coating on the medical device includes one or more base coatings and a top coating (see, e.g. U.S. Pat. No. 6,287,285). Optionally, the base coat has a binding component and a grafting component, and is used to adhere to the surface of the device and also to bond to the top coat. Specifically, the binding component binds to both the top coat and to the grafting component, and the grafting component adheres to the device surface. Typically, the base coat containing the grafting component and binding component in a suitable carrier such as a solution is first applied to the surface of the device. The base coat is preferably polymerized, e.g., exposed to polymerizing agent to polymerize the grafting component, and the grafting component is bonded to the binding component and adhered to the surface of the device to form a base coat on the device. The device is then coated with a top coat containing a desired bioactive agent. The top coat may be applied in a solution which is allowed to evaporate, to form a top coat with a bioactive agent. In another embodiment, the device is coated with a top coat comprising a linking agent, and the linking agent is exposed to the bioactive agent to form a complex therewith, to thereby form the bioactive coating of the invention. Because the top coat bonds to the base coat, the bioactive coating produced will not readily wear off.

In one embodiment, the base coat comprises a binding component which is a homofunctional compound having homofunctional groups which covalently bond to functional groups in the top coat. In a preferred embodiment, the homofunctional binding component is grafted to the grafting component by a hydrogen abstraction mechanism, in which the grafting component is activated by initiators and covalently bonds to the binding component. In another embodiment, the base coat comprises a binding component which is a heterofunctional compound having a first functional group for covalently bonding with the grafting component, and a second functional group for covalently bonding to functional groups in the top coat.

As mentioned above, in such illustrative embodiments of the invention the binding component of the base coat bonds to the top coat. In a specific embodiment, a bioactive agent has functional groups which directly bond to functional groups of the binding component. In another embodiment, the bioactive agent is bound to the binding component by a linking agent in the top coat. The linking agent may inherently have functional groups, or may be modified to include functional groups, which bond to functional groups of the binding component. The linking agent may be bound to the base coat and thereafter exposed to the bioactive agent, or alternatively, the linking agent may be exposed to the agent before or during the binding of the linking agent to the base coat.

A variety of suitable linking agents may be used to encapsulate and/or link components of the polymer matrix (e.g. the different polymers that comprise the various coating layers, the bioactive agents in the polymer matrices etc), including avidin-biotin complexes, and functionalized liposomes and microsponges and microspheres. Avidin is a polypeptide composed of at least 128 amino acid residues. Typically however, the single polypeptide chain is a subunit associated with three essentially identical polypeptide chains, forming a tetramer. Avidin as a receptor is typically used in conjunction with its highly specific ligand, biotin, $C_{10}H_{16}N_2O_3S$. An avidin tetramer will bind 4 biotin molecules in solution in a noncovalent interaction which has a binding constant of about $10^{15}$ $M^{-1}$, a half-life in vivo of about 89 days, and which is essentially undisturbed by organic solvents. Biotinylation, or the process of covalently binding biotin to another molecule, typically takes place by N-hydroxysuccinimide binding. Spacer molecules may be inserted between the avidin and the base coat, or between the biotin and the bioactive agent, as is known in the art, to facilitate avidin-biotin binding or improve the activity of the bioactive agent. The avidin or the biotin molecule may be chemically altered to decrease the binding constant, to thereby tailor the dissociation rate in vivo, and provide controlled release of the bioactive agent bound thereto. Avidin and biotin are available from a variety of commercial suppliers, such as Sigma. In one embodiment, avidin covalently binds to the binding component of the base coat, and binds to a biotinylated bioactive agent, such as a biotinylated protein, small molecule, peptide or oligonucleotide. However, the avidin-biotin linking agent may alternatively have biotin moieties covalently bound to the binding component of the base coat, and avidin moieties bound to the bioactive agent. Alternatively, biotin may be covalently bound to the base coat and to the bioactive agent, with avidin, by virtue of its multivalency with biotin, binding the two biotin moieties together.

Embodiments of the invention include devices having a plurality of coating layers having a plurality of therapeutic agents. In one such embodiment, a first bioactive agent is preferably mixed with the polymer, water, and crosslinking agent to form an aqueous dispersion or emulsion. In a preferred embodiment, the first agent is a biocidal agent. The polymeric emulsion or dispersion is then applied to the substrate to be coated and allowed to dry. A preferred method of drying is air drying. A second coating can be prepared by dissolving a second bioactive agent in water. In a preferred embodiment, the second agent is a lectin. In one method, the implant or article having the first dried coating is dipped in the lectin solution, taken out and allowed to air dry. The finished coating is subject to ambient temperature or elevated temperature drying in order to allow the lectin to bond to the polymer layer of the first coating composition.

Some methods according to the present invention are effective at relatively low temperatures, and particularly at ambient or room temperature, to allow for use with heat sensitive substrates, pharmaceutical agents and biomolecules. In one embodiment of the method according to the invention, the functional groups of the crosslinking agent are capable of reacting with the organic acid functional groups of the polymer in the first coating composition and the organic acid functional groups of the second coating at a temperature in the range of 10° C.-70° C., preferably at a temperature in the range of 15° C.-35° C. Such reactivity of the crosslinking agent makes it possible to coat the substrate at a temperature in the range of 10° C.-70° C., for example at a temperature in the range of 15° C.-35° C., such as at room temperature, although, of course, higher drying temperatures can be used if desired. The drying time will depend on the drying temperature, higher drying temperatures requiring shorter drying time and vice versa. However, it will be within the ordinary skill of a person skilled in the art to determine a suitable combination of drying temperatures and drying time for a specific coating.

One embodiment of the invention is a water insoluble polymeric layer having a first therapeutic agent admixed therein and able to be released under physiological temperature and pH. This embodiment of the invention also contains the crosslinking agent bonded to the polymeric material and having a substantial number of active functional groups remaining and capable of bonding additional material to the first layer. In one embodiment, the aqueous dispersion or emulsion includes polyurethane, a bioactive agent, and polyfunctional aziridine. A second coating or layer can be added to the first layer by preparing an aqueous solution or emulsion, optionally one that contains a second bioactive agent capable of being bound by the crosslinking agent.

According to the certain embodiments of the invention disclosed herein, bioactive agents are modified by chemically linking them to a high molecular weight, water-soluble polymer carrier. This modified agent is termed herein an agent-polymer conjugate. One special property of the agent conjugate is that the chemical linkage of the agent to the water-soluble polymer can be manipulated to hydrolytically degrade, thereby releasing biologically active agent into the environment in which they are placed.

The agent-polymer conjugates can be incorporated into a controlled release matrix, formulated from a second biocompatible polymer. When implanted into a tissue such as the intravascular space, the controlled-release matrix will release the agent-polymer conjugate which will release free agent molecules to treat the area of the tissue in the immediate vicinity of the polymer. The agent-polymer conjugates will also diffuse within the tissue, reaching a great distance from the matrix because of their low rate of clearance from the tissue. As the agent conjugates diffuse, the bond between the polymer and the agent will slowly degrade in a controlled, prespecified pattern, releasing the active agent into the environment in which they are placed to have its therapeutic effect. Similarly, agent-polymer conjugates can be administered directly to a tissue and the elimination rate will be reduced relative to free agent.

There are several important variables, all of which can be controlled to produce a final product that is best suited for treating a certain disease with specific kinds of agents. A first variable involves how the size and characteristics of the water-soluble polymer carrier can be varied. Either synthetic or naturally occurring polymers may be used. While not limited to this group, some types of polymers that might be used are polysaccharides (e.g. dextran, ficoll), proteins (e.g. polylysine), poly(ethylene glycol), or poly(methacrylates). Different polymers, because of their different size and shape, will produce different diffusion characteristics in the target tissue or organ.

Another variable is the specific nature of the hydrolytically labile bond between the water-soluble polymer and the agent (which, as is known in the art, can be varied). While not wishing to be limited to the following bonds, artisans can bond agents to water-soluble polymers using covalent bonds, such as ester, amide, amidoester, and urethane bonds. Artisans can also utilize ionic conjugates. By changing the nature of the chemical association between water-soluble polymer and agent, the half-life of carrier-agent association can be varied. This half-life of the agent-polymer conjugate in the environment in which it is placed can determine the rate of active agent release from the polymer and, therefore, the degree of penetration that the agent-polymer conjugate can achieve in the target tissue. Other suitable hydrolytically labile bonds which can be used to link the agent to the water soluble polymer include thioester, acid anhydride, carbamide, carbonate, semicarbazone, hydrazone, oxime, iminocarbonate, phosphoester, phophazene, and anhydride bonds.

The rate of hydrolytic degradation, and thus of agent release, can be also altered from minutes to months by altering the physico-chemical properties of the bonds between the agents and the polymer. The rate of release can be affected by (a) the nature of the bond, e.g., ionic, thioester, anhydride, ester, and amide links, in order of decreasing lability; (b) stereochetmical control, building in varying amounts of steric hindrance around the bonds which are to be hydrolyzed; (c) electronic control, building in varying electron donating/accepting groups around the reactive bond, controlling reactivity by induction/resonance; (d) varying the hydrophilicity/hydrophobicity of spacer groups between the agent and the polymer; (e) varying the length of the spacer groups, increasing length making the bond to be hydrolyzed more accessible to water; and (f) using bonds susceptible to attack by enzymes present in the environment in which the device is placed.

Another variable is the how the properties of the controlled release matrix can be varied, according to methods described in the art to vary the rate of polymeric agent conjugate release into the tissue (see, e.g. Saltzman, et al., 1991, Chemical Engineering Science, 46:2429-2444; Powell, et al., 1990, Brain Research, 515:309-311; Dang, et al., 1992, Biotechnology Progress, 8:527-532; Saltzman, et al., 1989, Biophysical Journal, 55:163-171; Radomsky, et al., 1992, Biology of Reproduction, 47:133-140; Saltzman, et al., 1992, Journal of Applied Polymer Science, 48:1493-1500; Sherwood, et al., 1992, Bio/Technology, 10: 1446-1449). Among the variables which affect conjugate release kinetics are: controlled release polymer composition, mass fraction of agent-polymer conjugate within the matrix (increasing mass fraction increases release rate), particle size of agent-polymer conjugate within the matrix (increasing particle size increases release rate), composition of polymeric agent conjugate particles (which can be varied by adding free agent agents or inert agents that influence particle solubility), and size (increasing surface area increasing the release rate), and shape (changing the pattern, e.g., first order, zeroth order, etc.) of the controlled release matrix. Suitable polymer components for use as controlled-release matrices include poly(ethylene-co-vinyl acetate), poly(DL-lactide), poly(glycolide), copolymers of lactide and glycolide, and polyanhydride copolymers.

A preferred embodiment of the invention includes the conjugation of a bioactive agent to a polymer via a hydrolytically labile bond to increase agent retention in a tissue, and, therefore increase the penetration distance of the bioactive agent in the tissue (see, also U.S. Pat. No. 6,545,681). Typically the bioactive agent conjugate is administered in a controlled-release matrix which comprises a biocompatible second polymer. Optionally the first polymer is water-soluble and the second polymer is not water-soluble. In this context, the polymer compositions of the invention comprise a polymer containing a functional group containing at least one hydrolyzable bond. Such polymer compositions include homo- and co-polymers and blends thereof (a copolymer or blend includes at least one other polymer which may or may not contain hydrolyzable bonds). By "hydrolyzable," "hydrolysis," and the like is meant the ability of water to chemically react with a substance to form two or more new substances. This typically involves ionization of the water molecule as well as splitting of the compound being hydrolyzed, e.g., an ester group of a polyester is hydrolyzed into the corresponding carboxylic acid and alcohol. By "acid-hydrolyzable bonds" and "base-hydrolyzable bonds" it is meant that the hydrolysis of the bond is initiated or catalyzed by an acidic or basic material, respectively. A bond may be both acid and base hydrolyzable. In addition, both types of bonds may be present in the polymer composition. The functional group containing hydrolyzable bonds may be present in the linear portions of the polymer chain (i.e., internal groups) or may be pendant to the polymer chain.

Exemplary functional groups which contain acid-hydrolyzable bonds include ortho-ester and amide groups. Exemplary functional groups which contain base-hydrolyzable bonds include α-ester and anhydride groups. Functional groups which contain both acid- and base-hydrolyzable bonds include carbonate, ester, and iminocarbonate groups. Thus, such exemplary polymers for use in the polymer compositions of the invention include polyesters, cellulose esters, polyester polyurethanes, polyamides, polycarbonates, and polyamino acids. A variety of other functional groups which contain labile bonds are known in the art and can be readily employed in the methods and compositions described herein (see, e.g. Peterson et al., Biochem. Biophys. Res. Comm. 200(3): 1586-1591 (1994) and Freel et al., J. Med. Chem. 43: 4319-4327 (2000)).

Optionally, the polymer composition further comprises pH-modifying compound. Optionally, the pH-modifying compound is a substantially water-insoluble. By "pH-modifying" is meant the ability of the compound to change the pH of an aqueous environment when the compound is placed in or dissolved in that environment. The pH-modifying compound is capable of accelerating the hydrolysis of the hydrolyzable bonds in the polymer upon exposure of the polymer composition to moisture and optionally heat. Suitable substantially water-insoluble pH-modifying compounds include substantially water-insoluble acids and bases. Inorganic and organic acids or bases may be used.

A variety of compositions and methods known in the art can be used to generate the compositions having functional groups which contain acid-hydrolyzable bonds disclosed herein. For example, in certain aspects, the present invention provides ortho ester lipids, and derivatives thereof, which upon certain pH conditions, undergo hydrolysis with concomitant or subsequent head group cleavage. As such, the present invention provides polymer compounds which include the compounds of Formula I as shown in U.S. Pat. No. 6,200,599. The compounds of Formula I typically comprise an ortho ester functionality or a derivative thereof In general, ortho ester functionalities are among the most sensitive moieties toward acid-induced hydrolysis, more acid labile than for instance, acetals or enol-ethers. Although the ortho esters of this embodiment of the invention are preferably bicyclic in nature, the compounds of Formula I are not limited as such. Preferably, upon a decrease in pH, the ortho esters of the present invention are (i) hydrolyzed and thereafter undergo (ii) intramolecular transesterification with concomitant or subsequent headgroup cleavage. In certain instances, such as when $R^2$ is an alkoxy group and $R^3$ is hydrogen, compounds of Formula I are not bicyclic. However, these compounds retain their 'self-cleaving' feature and ability to participate in the 2-step decomposition process discussed above. In Formula I, A and $A^1$ can be the same or different heteroatom. By changing the nature of the heteroatoms making up the ortho ester functionality, (e.g., replacing an oxygen atom with a sulfur atom) the ortho esters become susceptible to hydrolysis at varying pH. Thus, it is possible to tailor or program the pH value where hydrolysis of the ortho ester will occur. Moreover, incorporation of sulfur enables oxidative means of ortho ester hydrolysis via sulfoxide or sulfone intermediates.

As discussed in U.S. Pat. No. 6,300,458, hydroxypolycarbonates (HPC) offer to the biomedical area additional hydroxyl functional polymers that bind bioactive agents or carbohydrate polymers chemically or via hydrogen bonding to facilitate agent delivery and utility with subsequent biodegradability to acceptable byproducts. In a specific embodiment, the cyclic carbonate (CC) from the monoketal diol of pentaerythritol polymerized in $CHCl_3$ at 60° C. with $Et_2$ Zn catalyst in $CHCl_3$ at 60° C. in 4 hours to a quantitative yield of high molecular weight, crystalline polymer (PCC), melt peak 199° C. and Tg of 99° C. PCC is readily hydrolyzed with 80% acetic acid to the water-insoluble but water-swollen HPC, poly[5,5-bis(hydroxymethyl)-1,3-dioxan-2-one], with $M_w=3.1 \times 10^4$. HPC degrades completely in vitro in <16 hours in PBS-1X buffer (Ph 7.4, 37° C.) to pentaerythritol and presumably $CO_2$. This rapid degradation rate is decreased with random copolymers of HPC with CC, ε-caprolactone, or L-lactide. HPC and PCC may have important biomaterial applications as is and as the copolymers noted above or with ethylene oxide or other desirable comonomers. PCC and CC copolymers have properties attractive to the biomedical area as is or by conversion to the HPC product provided by hydrolysis or by in vivo enzymatic attack.

In this context, embodiments of the present invention include high weight average molecular weight (>5,000) polymers and copolymers of 5,5-bis(bydroxymethyl) 1,3-dioxan-2-one (hereinafter referred to as "BHMDO") and processes for manufacturing these polymers and copolymers. These polymers are biocompatible and useful for a variety of biomedical applications. Such homopolymers are crystalline and have a high melting point (ca 160-190° C.) which provides excellent mechanical properties. At the same time, they are hydrophilic and swellable by water (ca 100% at 37° C.), thereby enhancing biodegradability. The hydroxyl groups permit easy modification, an important advantage over non-hydrophilic biopolymers. For example, one can chemically bond a agent by an appropriate hydroxyl group reaction to form a hydrolytically labile bond or with a small peptide link cleavable by body enzymes along with a chemically bonded bioactive agent to target the anatomy with the appropriate agent. The hydroxyl groups provide hydrogen bonding with carbohydrate polymers, including nucleic acids, and proteins, which also facilitate direction of these polymers, as is or modified, to specific cites for therapeutic purposes. Properties can be varied widely via copolymers (generally from about 1% up to about 99% BHMDO) to change properties and permit diverse biomedical applications.

Related embodiments of the present invention provide erodible yet biocompatible polymers with desirable mechanical properties. In this context, the polymers HPC and PLC may also be attractive materials for temporary scaffolds or coatings. A feature of these polymers is their tendency to undergo surface erosion. Heterogeneous hydrolysis theoretically would better preserve the mechanical strength and physical integrity of the matrix during biodegradation, which is highly desirable in terms of predictable performance. To maximize control over the release process, it is desirable to have a polymeric system which degrades from the surface and deters the permeation of the agent molecules. Achieving such a heterogeneous degradation requires the rate of hydrolytic degradation on the surface to be much faster than the rate of water penetration into the bulk. A preferable embodiment is a polymer composition having a hydrophobic backbone and a water labile linkage.

As noted above, the polymer compositions disclosed herein allow for the controlled release of bioactive agents. This controlled release can be modulated by a number of factors including the diffusion coefficient of the polymer matrix as well as the pH of the environment in which the polymer compositions function. In this context, one of the embodiments of the invention includes a method for the controlled release of a biologically active agent wherein the agent is released from a hydrophobic, pH-sensitive polymer matrix (see also U.S. Pat. No. 6,306,422). In one embodiment, a polymer of hydrophobic and weakly acidic comonomers is disclosed for use in the controlled release system., In a specific embodiment, weakly basic comonomers are used and the active agent is released as the pH drops. For example a medical device coated with a pH-sensitive polymer having an antibiotic trapped within its matrix can release the active agent when exposed to a higher pH environment as the polymer gel swells. Such release can be made slow enough so that the bioactive agent remains at significant levels for a clinically useful period of time.

Related embodiments of the invention provide additional compositions and method for releasing a bio-active agent or a agent within a biological environment in a controlled manner. One such composition is a dual phase polymeric agent-delivery composition comprising a continuous biocompatible gel phase, a discontinuous particulate phase comprising defined microparticles and an agent to be delivered (see, e.g. U.S. Pat. No. 6,287,588). Typically in such embodiments, a microparticle containing a bio-active agent is releasably entrained within a biocompatible polymeric gel matrix. The bio-active agent release may be contained in the microparticle phase alone or in both the microparticles and the gel matrix. The release of the agent is prolonged over a period of time, and the delivery may be modulated and/or controlled. In addition, a second agent may be loaded in some of the microparticles and/or the gel matrix.

In such embodiments of the invention, a main mechanism of in vivo degradation of the polymers is by hydrolytic degradation in which endogenous enzymes may also play a role (see, e.g. Meyers et al., J. Med. Chem. 2000, 43, 4319-4327). Important factors influencing hydrolytic degradation include water permeability, chemical structure, molecular weight, morphology, glass transition temperature, additives, and other environmental factors such as pH, ionic strength, site of implantation, etc. The duration of sustained delivery can be adjusted from few days up to one year by a person of ordinary skill in the art through proper selection of polymer and fabrication method.

Embodiments of the invention include those in which the release of one or more biologically active agents is multiphasic. For example, this release can comprise an initial burst or, immediate release of an agent present at or near the surface of the coating layer, a second phase during which a release rate is slow or sometime no bio-active agent is released, and a third phase during which most of the remainder of the biologically active agent (or another bioactive agent) is released as erosion proceeds. Any agent, as long as it is suitable for incorporation into a polymer matrix (e.g. via microencapsulation in a microparticle), as is known in the art, can utilize the delivery system described by the current invention.

Specific embodiments of the invention include bioactive agents that are incorporated in microparticles. Since the polymeric gel and/or microparticle of the delivery system of the invention are preferably biocompatible and biodegradable, there is minimal toxic effect and irritation to the host. The agent release profile can be controlled and improved by proper design and preparation of various gel forming polymers or copolymer blocks. The release profile of the polymeric gel may also be modified through preparation of a gel blend by selection of individual gel systems and ratios of individual gel systems in the blend. Agent release is also controllable through adjustment of the concentration of the gel blends in the agent delivery liquid. Additional or second agents can also be loaded into the microparticles and/or the polymeric gel matrix. The additional agent can be a regulatory agent for the microparticle and/or the gel, or a second bio-active agent to be released into the biological environment in a same or different release rate. In such embodiments, a consideration as to how much agent can be loaded into the microparticle and how much of such agent carrying microparticle can be loaded into the polymeric gel is one of functionality, namely, the agent/microparticle load may be increased until the microparticle structure, and/or the gelation properties of the polymer or copolymer are adversely affected to an unacceptable degree, or until the properties of the system are adversely affected to such a degree as to make administration of the system unacceptably difficult. Generally speaking, about 0.0001 to 30% by weight of a agent can be loaded into a microparticle with 0.001 to 20% being most common. The agent carrying microparticle will generally make up between 0.0001 to 30% by weight of the formulation with ranges of between about 0.001 to 20% being most common. These ranges of agent/microparticle loading are not limiting to the embodiments of the invention. Provided functionality is maintained, agent loadings outside of these ranges fall within the scope of the invention.

As noted above, this invention is applicable to bio-active agents of all types including lectins and growth inhibitory agents. In some instances, the functionality or physical stability of bioactive agent can also be increased by the addition of various additives to aqueous solutions or suspensions of the polypeptide or protein agent. Additives, such as polyols (including sugars), amino acids, surfactants, polymers, other proteins and certain salts may be used. These additives can readily be incorporated into the microparticle/polymer gel system of the present invention, which will then undergo a gelation process.

In addition to the microparticles disclosed above, additional agents such as liposomes can be used to control the release of bioactive agents from the disclosed polymer compositions. Liposomes are lipid molecules formed into a typically spherically shaped arrangement defining aqueous and membranal inner compartments. Liposomes can be used to encapsulate compounds such as bioactive agents within the inner compartments, and deliver such agents to desired sites within a patient. The agents contained by the liposome may be released by the liposome and incorporated into the patient's cells, as for example, by virtue of the similarity of the liposome to the lipid bilayer that makes up the cell membrane. A variety of suitable liposomes may be used, including those available from NeXstar Pharmaceuticals, Alkermes or Liposome, Inc, if functionalized as by the procedures described herein.

In addition to liposomes, microsponges can be used to control the release of bioactive agents from the disclosed polymer compositions. Microsponges are high surface area polymeric spheres having a network of cavities which may contain compounds such as bioactive agents. The microsponges are typically synthesized by aqueous suspension polymerization using vinyl and acrylic monomers. The monomers may be mono or bifunctional, so that the polymerized spheres may be cross-linked, thus providing shape stability. Process conditions and monomer selection can be varied to tailor properties such as pore volume and solvent swellability, and the microsponges may be synthesized in a controlled range of mean diameters, including small diameters of about 2 micrometers or less. A standard bead composition would be a copolymer of styrene and di-vinyl benzene (DVB). The agents contained by the polymeric microsponges may be gradually released therefrom within the patient due to mechanical or thermal stress or sonication. A variety of suitable microsponges may be used, including those available from Advanced Polymer Systems, if functionalized as by the procedures described herein.

An alternative embodiment includes a device containing reservoirs loaded with the bioactive agent (see, e.g. U.S. Pat. No. 6,273,913). In such embodiments, a polymer coating of the invention is applied over the reservoirs to control the diffusion of the drug from the reservoirs to the desired site within the body (e.g. the artery wall). One advantage of this system is that the properties of the coating can be optimized for achieving superior biocompatibility and adhesion properties, without the addition requirement of being able to load and release the drug. The size, shape, position, and number of reservoirs can be used to control the amount of drug, and therefore the dose delivered.

Yet another embodiment of the invention utilizes oscillating chemical systems to modulate the release of bioactive agents (see, e.g. U.S. Pat. No. 6,068,853). By taking advantage of oscillating chemical systems, one can change the state, i.e. the pH, of a solution, a bioactive drug, enhancer or solubilizer resulting in oscillating the ability of an active ingredient to be delivered. The pH of a solution can be oscillated over a range of pH values from 2 to 10 by the reduction and oxidation (redox) reactions of salts, such as permanganates, iodates, sulfates, chlorates, or bromates. Upon activation, the delivery system conditions begin to oscillate and with it, the delivery of the active agent oscillates.

In general, the present invention control of an active agent can be seen with specific reference to pH and/or redox oscillating reactions. However, any other oscillating species in an oscillating reaction can advantageously be employed in a similar fashion. With reference to oscillating systems in pharmaceutical contexts, the environment of the active agent to be delivered can have its state, i.e. pH, altered between a value where the active agent shifts between species which more readily and less readily permeates or diffuses through a delivery device barrier; a membrane barrier through which the active agent must pass or a matrix from which the active agent must be released can have its permeability altered in response to oscillation changes; a barrier separating a flux enhancer from the active agent can be modulated to regulate the amount of flux enhancer delivered to the active agent and as a result modulate the flux enhancer dependent active agent delivery; a polymer can be modulated to shift between a more viscous and less viscous form (i.e. poly-.gamma.-glutamate as in Creacenzi et al., Polymer Preprints, August 1994, 407-408) or a more solubilized and less solubilized form or a more swollen and a less swollen form (i.e. poly(meth)acrylic acid as in Kou et al., Pharmaceutical Research 5, #9, 1988, 592-597), thereby altering the amount of water available to the active agent or another membrane which either needs to be or needs not to be hydrated in order to have proper active agent delivery, etc.

Where a lipophilic membrane is involved, either as part of the delivery device or as a membrane of the patient through which the active agent must pass (and is not changed by the environment through which it passes after leaving the device and before arriving at the lipophilic membrane), the combination of an active agent, preferably a agent, with a chemical oscillating reaction, may render the active agent charged or uncharged relative to its own pKa value. Since only the uncharged form of a drug can permeate across lipophilic membranes, a periodic delivery profile may be obtained by oscillating the state, i.e. pH, of the drug solution. The same type of end result can be achieved by oscillating the permeability of a membrane to either the active agent per se or to a flux enhancer needed for active agent delivery.

Exemplary Coated Devices

Essentially any medical device which experiences biofilm formation and/or encrustation is appropriate for the practice of the present invention, including drug delivery devices such as insulin pumps, devices which augment heating such as cochlear implants, urine contacting devices (for example, urethral stents, urinary catheters), blood contacting devices (including cardiovascular stents, venous access devices, valves, vascular grafts, hemodialysis and biliary stents), and body tissue and tissue fluid contacting devices (including biosensors, implants and artificial organs). Medical devices include but are not limited to permanent catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts, cerebral and spinal shunts, heart valves, heart assist devices (e.g., left ventricular assist devices), pacemaker capsules, incontinence devices, penile implants, small or temporary joint replacements, urinary dilator, cannulae, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field. Medical devices also include any device which may be inserted or implanted into a human being or other animal, or placed at the insertion or implantation site such as the skin near the insertion or implantation site, and which include at least one surface which is susceptible to colonization by biofilm embedded microorganisms. Medical devices also include any other surface which may be desired or necessary to prevent biofilm embedded microorganisms from growing or proliferating on at least one surface of the medical device, or to remove or clean biofilm embedded microorganisms from the at least one surface of the medical device, such as the surfaces of equipment in operating rooms, emergency rooms, hospital rooms, clinics, and bathrooms.

The medical devices may be formed of any suitable metallic materials or non-metallic materials known to persons skilled in the art. Examples of metallic materials include, but are not limited to titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex (polytetrafluoroethylene), Dacron™ (polyethylene tetraphthalate), Teflon (polytetrafluoroethylene), latex, elastomers and Dacron™ sealed with gelatin, collagen or albumin, and derivatives or combinations thereof. The medical devices include at least one surface for applying the biofilm inhibiting composition. Preferably, the biofilm inhibiting composition is applied to the entire portion of the medical device that is accessible to biofilm forming organisms.

As shown above, the polymer compositions of the present invention are useful with a variety of implantable devices. The present invention depends not on the configuration of the implantable device, but rather on the use of the inventive membranes to cover or encapsulate the device elements. Preferred embodiments of the present invention include a therapeutic, biocompatible coating over the susceptible surface of a device substrate. The term "susceptible surface" as used herein refers to any surface whether in an industrial or medical setting, that provides an interface between an object and the fluid. A surface, as understood herein further provides a plane whose mechanical structure, without further treatment, is compatible with the adherence of microorganisms. Microbial growth and/or biofilm formation with health implications can involve those surfaces in all health-related environments.

Susceptible surfaces further include the inner and outer surfaces of pieces of medical equipment, medical gear worn or carried by personnel in the health care settings and protective clothing for biohazard or biological warfare applications. Such surfaces can include counter tops and fixtures in areas used for medical procedures or for preparing medical apparatus, tubes and canisters used in respiratory treatments, including the administration of oxygen, solubilized drugs in nebulizers, and anesthetic agents. Additional surfaces include those surfaces intended as biological barriers to infectious organisms such as gloves, aprons and faceshields.

Surfaces in contact with liquids are particularly prone to microbial growth and/or biofilm formation. As an example, those reservoirs and tubes used for delivering humidified oxygen to patients can bear biofilms inhabited by infectious agents. Dental unit waterlines similarly can bear biofilms on their surfaces, providing a reservoir for continuing contamination of the system of flowing and aerosolized water used in dentistry.

In accordance with the invention, a method for preventing, inhibiting or eliminating the growth, dissemination and/or accumulation of microorganisms on a susceptible surface (including but not limited to the formation of biofilms) comprises the step of contacting such surface with an composition of the invention, with an amount sufficient to prevent, inhibit or eliminate such growth, dissemination and/or accumulation, i.e., with an effective amount.

The hydrogels described herein are particularly useful with a variety of implantable devices for which it is advantageous to provide a surrounding water layer. Glucose sensors which utilize, for example, glucose oxidase to effect a reaction of glucose and oxygen are known in the art, and are within the skill in the art to fabricate. See, for example, U.S. Pat. Nos. 5,165,407, 4,890,620, 5,390,671 and 5,391,250, the disclosures of each being incorporated herein by reference. For example, sensors for monitoring glucose concentration of diabetics are described in Shichiri, et al., "In Vivo Characteristics of Needle-Type, Glucose Sensor-Measurements of Subcutaneous Glucose Concentrations in Human Volunteers," Horm. Metab. Res., Suppl. Ser. 20:17-20 (1988); Bruckel, et al., "In Vivo Measurement of Subcutaneous Glucose Concentrations with an Enzymatic Glucose Sensor and a Wick Method," Klin. Wochenschr. 67:491-495 (1989); and Pickup, et al., "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

While drug delivery devices (e.g. insulin pumps) and cochlear implants are discussed as preferred devices for use with the polymer coatings disclosed herein, artisans understand that the polymer compositions can be utilized with a wide variety of devices known in the art such as those discussed above.

Various citations are referenced throughout the specification (e.g. U.S. Pat. No. 6,475,434 or U.S. patent application Ser. No. 20030031644). In addition, certain text from related art is reproduced herein to more clearly delineate the various embodiments of the invention. The disclosures of all citations in the specification are expressly incorporated herein by reference.

The invention claimed is:

1. A medical device having a surface coated with a composition comprising a lectin, wherein:
   (a) the medical device includes a metallic material;
   (b) the lectin binds a compound produced by a microorganism capable of forming a biofilm on the surface of the medical device so as to enhance attachment of the microorganism to the composition comprising the lectin; and
   (c) the lectin is disposed within a biodegradable polymer composition that can slough away from the surface of the medical device when the lectin is bound to the compound produced by a microorganism,
   so as to inhibit formation of a biofilm on the surface of the medical device.

2. The medical device of claim 1, wherein the biodegradable polymer is a biocompatible polymer that degrades at a controllable rate within an in vivo environment.

3. The medical device of claim 1, wherein the composition further comprises at least one agent that inhibits the growth of the microorganism.

4. The medical device of claim 3, wherein the agent is an antibiotic or an antifungal agent.

5. The medical device of claim 1, wherein the lectin binds to a compound produced by a microorganism selected from the group consisting of *Pseudomonas aeruginosa*, *Streptococcus pneumoniae*, *Streptococcus viridans*, *Haemophilus influenzae*, *Escherichia coli*, *Staphylococcus aureus*, *Staphylococcus epidermidis* and *Candida albicans*.

6. The medical device of claim 1, wherein the lectin is wheat germ agglutinin or concanavalin A.

7. The medical device of claim 1, wherein the device is implantable.

8. The medical device of claim 7, wherein the device comprises a drug delivery pump, a pacemaker, a cochlear implant, a shunt, a catheter or a cannula.

9. The medical device of claim 1, wherein the metallic material is titanium or stainless steel.

10. The medical device of claim 1, wherein the medical device further includes a biostable polymeric material.

11. A medical device having a surface coated with a composition comprising a lectin, wherein:
    (a) the surface of the medical device includes a biostable polymeric material;
    (b) the lectin binds a compound produced by a microorganism capable of forming a biofilm on the surface of the medical device so as to enhance attachment of the microorganism to the composition comprising the lectin; and
    (c) the lectin is disposed within a biodegradable polymer composition that can slough away from the biostable polymeric material when the lectin is bound to the compound produced by a microorganism, so as to inhibit formation of a biofilm on the surface of the medical device.

12. The medical device of claim 11, wherein the biostable polymeric material comprises polytetrafluoroethylene.

13. The medical device of claim 11, wherein the medical device further includes a metallic material.

14. The medical device of claim 1 or claim 11, wherein the composition comprising the lectin is disposed on a region of the device having a mechanical structure that is compatible with the adherence of microorganisms.

* * * * *